US00PP09866P

United States Patent [19]

Chandler

[11] Patent Number: Plant 9,866

[45] Date of Patent: Apr. 22, 1997

[54] STRAWBERRY PLANT CALLED 'ROSA LINDA'

[75] Inventor: Craig K. Chandler, Temple Terrace, Fla.

[73] Assignee: Florida Foundation Seed Producers, Inc., Greenwood, Fla.

[21] Appl. No.: 528,541

[22] Filed: Sep. 15, 1995

[51] Int. Cl.[6] ..... A01H 5/00

[52] U.S. Cl. ..... Plt./49

[58] Field of Search ..... Plt./48, 49

[56] References Cited

U.S. PATENT DOCUMENTS

P.P. 5,266 7/1984 Bringhurst et al. ..... Plt./49

P.P. 6,578 1/1989 Votho et al. ..... Plt./48

P.P. 8,729 5/1994 Howard ..... Plt./48

*Primary Examiner*—James R. Feyrer

*Attorney, Agent, or Firm*—William M. Hobby, III

[57] ABSTRACT

A new and distinct variety of strawberry (*Fragaria×ananassa*), which originated from a hand-pollinated cross between two University of Florida breeding selections, FL 87-418 and FL 87-200. The new strawberry is distinguished by its upright plant habit and the shape, appearance, and flavor of its fruit.

2 Drawing Sheets

SUMMARY OF THE INVENTION

A new and distinct variety of strawberry (*Fragaria× ananassa*) originated from a hand pollinated cross between two University of Florida breeding selections, FL 87-418 and FL87-200, made at the University of Florida's Gulf Coast Research & Education Center at Dover, Fl. The seeds resulting from the controlled hybridization were germinated in a greenhouse and the resulting seedlings were planted and allowed to produce daughter plants by asexual propagation by runners. Two daughter plants from each seedling were transplanted to raised beds. These plants later fruited at the Gulf Coast Research & Education Center at Dover, Florida and one pair of specimens of one plant was selected for its outstanding fruit qualities. The new variety, FL 90-15, has been asexually propagated by runners annually and further test plantings have established that during asexual multiplication, the vegetative and fruit characteristics of the original plants are maintained. The new strawberry, called 'Rosa Linda', is distinguished by its more upright petioles and the shape, appearance, the flavor of its fruit.

BRIEF DESCRIPTION OF THE PHOTOGRAPHS

The accompanying photographs show typical specimens of the fruit and leaves of the new variety in color.

DETAILED DESCRIPTION OF THE NEW VARIETY

Figure 1:
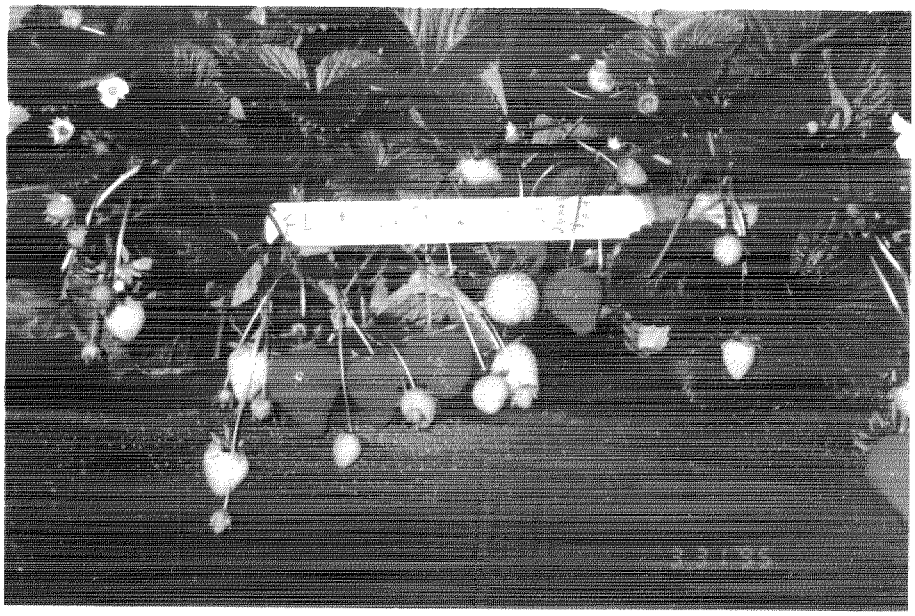
FIG. 1 is a photograph of the present strawberry plant.
Figure 2:
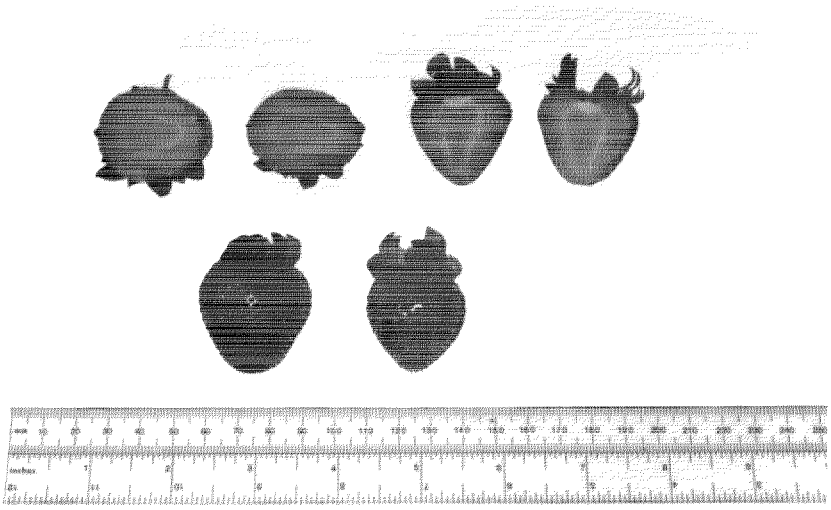
FIG. 2 is a photograph of whole and cut pieces of fruit shown with a ruler.
Figure 3:
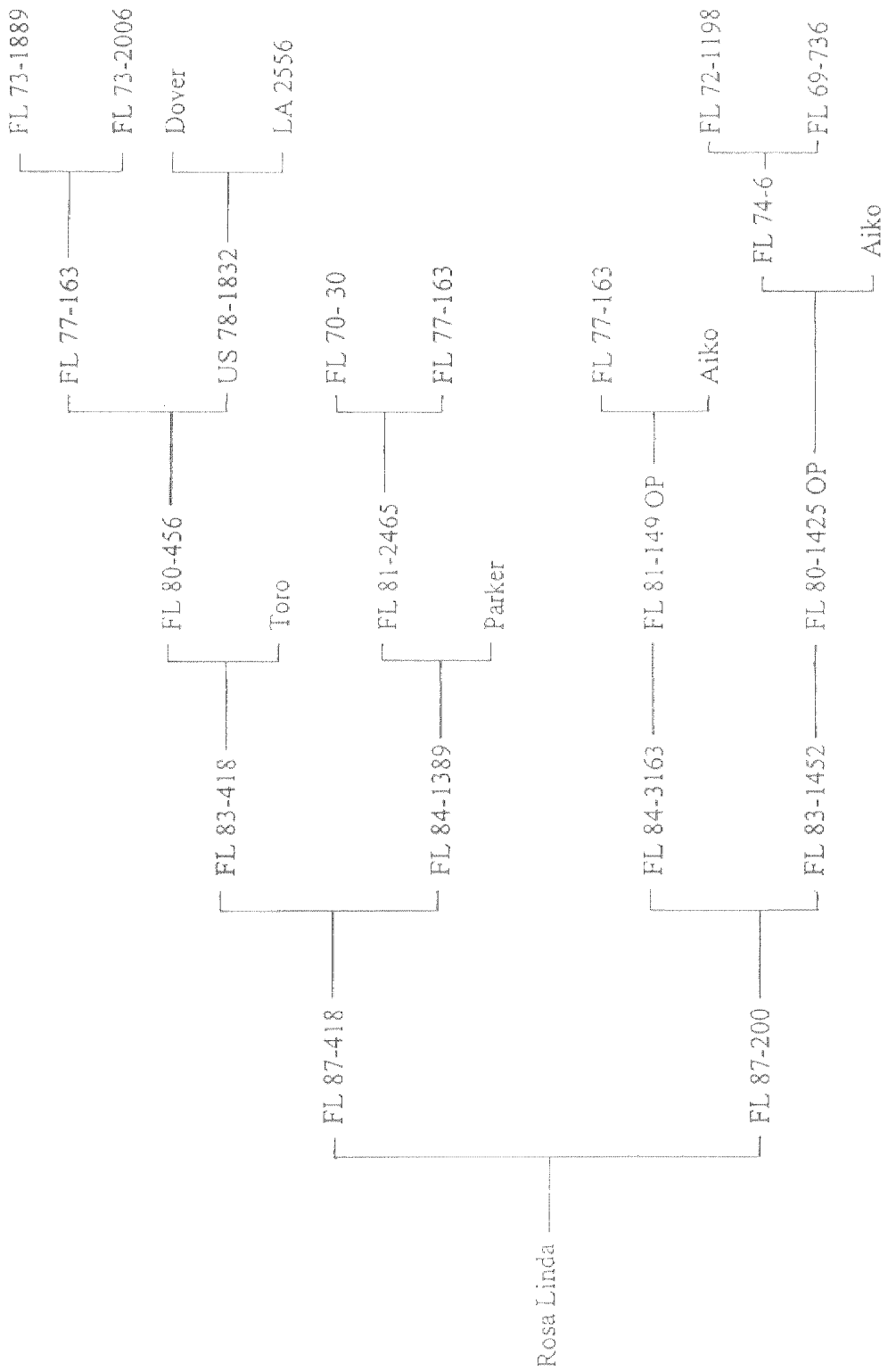
FIG. 3 is a pedigree chart.

The following is a detailed description of the pomological characteristics of the subject strawberry. Where dimensions, sizes, colors, and other characteristics are given, it is to be understood that such characteristics are approximations of averages set forth as accurately as practicable. The present strawberry (*Fragaria×ananassa*) resulted from a cross between FL 87-418 and FL 87-200, which were two advanced selections from the University of Florida strawberry breeding program. As shown in pedigree chart of FIG.

3, FL 87-418 is a cross between FL 83-418 and FL 84-1389 and FL 87-200 is cross between FL 84-3163 and FL 83-1452 of the University of Florida strawberry breeding program. The description reported herein is from specimens grown at the Gulf Coast Research & Education & Research Center at Dover, Fl. Where applicable, Rosa Linda is compared to Sweet Charlie, Oso Grande, and Selva (currently the standard strawberry varieties grown in Florida).

Type: Short day.

Size of plant: Medium to large (28 cm high×30 cm wide×30 cm deep for a typical, mature plant in a fruit production field); upright in appearance. Rosa Linda is similar to Sweet Charlie in the production and timing of its runners but it appears to produce fewer runners than Sweet Charlie in hot weather (greater than 32° C.). Supplement chilling is not needed for Rosa Linda to perform well in central Florida. Like Sweet Charlie, Rosa Linda begins to initiate flower buds soon after being exposed to average daily temperatures of 21° C. or lower in the early fall.

Leaves: Petioles are similar in length to those of Sweet Charlie, but are stiffer. Relatively few of the petioles have bract leaflets compared to the petioles of Sweet Charlie or Oso Grande. Leaflets are generally flatter and when growing in a nursery have a slightly darker green (L=36.3, a=−13.3, b=+18.0 [L a b color notation system]) appearance than those of Sweet Charlie. The leaf color of the top surface is about the same as those of Oso Grande (Munsell 5 GY 4/3). The central leaflet has a cuneate base while the side leaflets have oblique bases. The length of mature leaflets varies from 55 to 70 mm; the width from 60 to 70 mm. Leaflet margins are rounded dentate with 22 to 29 serrations per leaflet. The serrations are smaller, and generally more numerous, than the serrations on the leaflets of Sweet Charlie. The texture of the upper leaflet surface is rugose and feels rougher than the leaflets of Sweet Charlie. The petioles tend to be more upright than those of Sweet Charlie or Oso Grande which generally makes the fruit more visible.

Flowers: Flowers open at or below canopy height. Flowers typically have 5 to 7 petals and are completely self-fertile with ample pollen throughout the season. Calyx lobes are mostly entire and recurved. The calyx is medium to large but generally smaller than the calyx on Sweet Charlie fruit. The calyx is positioned even with or slightly below the shoulder of the fruit.

Fruit: Primary fruit are variable in shape; secondary and later fruit are typically conically shaped. Mature fruit frequently has white tips early in the season, but otherwise ripening is uniform. External fruit color is bright red with a deeper red blush around the achenes. The skin color of the fruit is darker than that of Sweet Charlie, but about the same as that of Oso Grande. The internal color of the fruit is mostly bright red but darker than the internal color of Sweet Charlie or Oso Grande. Ripe fruit is moderately firm (similar to Sweet Charlie) and has a vitamin C concentration of approximately 45 mg/100 g FW (which is less than the concentration of vitamin C in Sweet Charlie fruit, but more than the concentration in Oso Grande fruit), and has an average berry weight of 17 grams (similar to Sweet Charlie, but having a smaller average size than Oso Grande). A relatively low percentage (2%) of the total anthocyanins in the fruit is cyanidin pigment compared to 13% for Oso Grande, 6% for Selva and 4% for Sweet Charlie. Small, unmarketable fruit is produced from the terminal flowers of the inflorescence. The fruit has a flavor that is comparable to the fruit of Sweet Charlie but is usually slightly less sweet than Sweet Charlie fruit, and has a hint of a rose aroma. The achenes are greenish yellow and are slightly recessed. Primary fruit are wedge to conical in shape and represent about 14% of the marketable fruit harvested. The medium-sized (15–20 g) conically shaped berries are ideal for packaging in pint clamshell-type containers. Most of the primary, secondary and tertiary fruit are marketable since there are usually relatively few misshapen or water damaged fruit.

Productivity: Medium to high (23–35 Mt/ha); greater early season (December through February) fruit yield than Oso Grande, but not greater than Sweet Charlie. The plant is recommended for commercial use in west central Florida and other area with mild winter climates because of its ability to produce high early season (December–February) yields of attractive, flavorful fruit. A planting date of Oct. 15–20 and a plant spacing of 40–46 cm between plants within a row has been found to produce the best performance in central Florida. Fruit yields of strawberry clones in GCREC-Dover Row Trails in 1995 and 1996 (through Mar. 25, 1996) has produced the following comparative yields:

| | Yield in flats per acre (4.65 kg of fruit per flat) | | | | |
|---|---|---|---|---|---|
| | December | January | February | March | Total |
| Rosa Linda | 232 | 259 | 821 | 856 | 2168 |
| Sweet Charlie | 290 | 401 | 994 | 602 | 2287 |
| Selva | 219 | 437 | 176 | 754 | 1586 |
| Oso Grande | 76 | 361 | 557 | 785 | 1779 |

Pest responses: Appears to be more resistant to Phomopsis leaf blight and fruit rot, angular (bacterial) leaf spot, and Botrytis fruit rot than is Sweet Charlie, and more resistant to powdery mildew and two spotted spider mite than Selva. Rosa Linda does show moderate susceptibility to anthracnose crown and fruit rot.

Isozyme comparison: Rosa Linda can be separated from Sweet Charlie, Oso Grande, and selva on the basis of PGI and LAP isozyme banding patterns. Rosa Linda has the $A_2$ from of PGI and the $B_1$ form of LAP, while Sweet Charlie has the $A_1$ and $B_1$, Oso Grande the $A_2$ and $B_3$, and Selva the $A_2$ and $B_3$ forms of PGI and LAP respectively as follows.

| | Rosa Linda | Sweet Charlie | Oso Grande | Selva |
|---|---|---|---|---|
| PGI | A2 | A1 | A2 | A2 |
| LAP | B1 | B1 | B3 | B3 |

Distinctive features: The most distinctive features of the variety are 1) the consistency of shape and appearance of its secondary and later fruit, 2) its generally upright plant habit, and 3) the unique aromatic quality of its fruit.

I claim:

1. A new and distinct variety of strawberry plant, substantially as illustrated and described, characterized by its upright plant habit and the visual and flavor qualities of its fruit.

* * * * *